United States Patent [19]
Thangaraj et al.

[11] Patent Number: 6,087,514
[45] Date of Patent: Jul. 11, 2000

[54] TITANIUM SILICATE MOLECULAR SIEVE OXIDATION CATALYSTS AND THE PRODUCTION THEREOF

[75] Inventors: Appadurai Thangaraj, Colonia; Steven M. Kuznicki, Whitehouse Station; Gerald S. Koermer, Roseland, all of N.J.

[73] Assignee: Engelhard Corporation, Iselin, N.J.

[21] Appl. No.: 09/175,264

[22] Filed: Oct. 20, 1998

[51] Int. Cl.$^7$ .......................... B01J 29/70; C07D 301/12
[52] U.S. Cl. .............................. 549/531; 502/60; 502/64; 502/85; 502/86; 423/713; 549/513; 549/518; 549/512; 549/524
[58] Field of Search ................... 502/60, 64, 85, 502/86; 423/713; 549/512, 513, 518, 524, 531

[56] References Cited

U.S. PATENT DOCUMENTS

| | | | |
|---|---|---|---|
| 3,329,481 | 7/1967 | Young . | |
| 4,853,202 | 8/1989 | Kuznicki | 423/326 |
| 4,892,720 | 1/1990 | Skeels et al. | 423/328 |
| 5,208,006 | 5/1993 | Kuznicki | 423/713 |
| 5,244,650 | 9/1993 | Kuznicki | 423/718 |
| 5,453,263 | 9/1995 | Blosser et al. | 423/713 |
| 5,527,520 | 6/1996 | Saxton et al. | 423/706 |
| 5,656,252 | 8/1997 | Tuel et al. | 423/705 |
| 5,869,706 | 2/1999 | Dartt et al. | 549/531 |
| 5,906,954 | 5/1999 | Koermer | 502/60 |
| 5,958,369 | 9/1999 | Kosuge et al. | 423/705 |
| 5,977,009 | 11/1999 | Faraj | 502/64 |

OTHER PUBLICATIONS

M.W. Anderson, A. Phillippou, Z. Lin, A. Ferreira and J. Rocha; Angew. Chem. Int. Engl., 34, 1003 (1995) "Al, Ti Avoidance in the Microporous Titanoaluminosilicate ETAS–10".

Rocha, Z. Lin, A. Ferreira and M.W. Anderson; J. Chem. Soc. Chem. Commun., 867 (1995) "Ga, ti Avoidance in the Microporous titanogallosilicate ETGS–10".

Primary Examiner—Tom Dunn

[57] ABSTRACT

Disclosed are novel crystalline molecular sieves having the framework of ETS-10 titanium silicate which contain both octahedral and tetrahedral titanium atoms and are in acid form. The sieves are prepared by adding a complexing agent such as hydrogen peroxide during synthesis or by treating a synthesized titanium silicate molecular sieve with a reagent that replaces tetrahedral silicon with tetrahedral titanium atoms.

19 Claims, No Drawings

TITANIUM SILICATE MOLECULAR SIEVE OXIDATION CATALYSTS AND THE PRODUCTION THEREOF

FIELD OF THE INVENTION

The invention relates to novel crystalline titanium silicate molecular sieves containing acid sites and both tetrahedrally and octahedrally coordinated titanium atoms in the molecular sieve framework. These materials are useful as sorbents and as catalysts for oxidation reactions. This invention relates also to novel methods for preparing such catalysts and to the use thereof in oxidation reactions, especially partial oxidation reactions.

BACKGROUND OF THE INVENTION

The goal of incorporating tetrahedral titanium(IV) in classical zeolite structures has been actively pursued for more than a decade. Such materials include tetrahedral titanium incorporated into ZSM-5 analogs such as TS-1, substitution into ZSM-11 analogs such as TS-2, substitution into zeolite Beta and, more recently, incorporation into MCM-41. This interest results from the unique catalytic properties of Ti(IV) sites in molecular sieve configurations.

Commercially, the hydroxylation of phenol to catechol and hydroquinone is practiced using TS-1. Other reactions which have demonstrated promise include oximation of cyclohexanone as well as olefin epoxidation, especially the conversion of propylene to propylene oxide. A potentially important commercial reaction involving the rearrangement of oxime to lactam has also been reported.

The known examples of tetrahedral Ti (IV) in zeolite structures have several elements in common. First, the amount of Ti incorporation is relatively low, typically 2–3 wt % or less. Second, zeolites such as TS-1, Ti-Beta, Ti-MCM-41 etc., are silica rich; i.e., there are only low levels of framework aluminum in these zeolites. This means that the ion-exchange capacity and the potential acid concentration, (the number of potential acid sites), in these zeolites is low. The low level of ion-exchange sites in zeolites with tetrahedral Ti incorporation means that the ion-exchange properties, the adsorptive properties and potential catalytic applications are also restricted.

In contrast, the materials of this invention combine relatively high levels of tetrahedral Ti incorporation with high levels of ion-exchange capacity. This high ion-exchange capacity arises from framework charge neutralization associated with octahedrally coordinated framework titanium atoms. Each octahedral titanium atoms results in two negative framework charges which must be neutralized with cations or other appropriate species.

ETS-10 molecular sieve (U.S. Pat. No. 4,853,202) is a crystalline structure consisting of silica chains linked to octahedral titania chains. As such, it contains both tetrahedral and octahedral framework sites.

Reference is made to the following:

S. M. Kuznicki and K. A. Thrush; U.S. Pat. No. 5,244,650 and U.S. Pat. No. 5,208,006.

M. W. Anderson, A. Philippou, Z. Lin, A. Ferreira and J. Rocha; Angew. Chem. Int. Engl., 34, 1003 (1995).

Rocha, Z. Lin, A. Ferreira and M. W. Anderson; J. Chem. Soc. Chem. Commun., 867 (1995).

In U.S. Pat. No. 3,329,481 the synthesis of charge bearing titanium silicates using a peroxy reagent during synthesis is disclosed. Distinctions between the resulting "titanium zeolites" and ETS-10 molecular sieve are set forth in detail in U.S. Pat. No. 5,244,650.

U.S. Pat. No. 5,208,006, commonly assigned, discloses and claims a host of crystalline titanium molecular sieves of the ETS-10 type having at least one octahedrally coordinated site comprising titanium and at least tetrahedrally coordinated silicon. The tetrahedral sites may include, in addition to silicon, any one of a host of metals, one of which may be titanium. The terms "octahedral coordination" and "tetrahedral coordination" are defined in U.S. Pat. No. 5,208,006 at col. 19. The teachings of U.S. Pat. No. 5,208,006 are incorporated herein in full by cross-reference.

Unlike other atoms, the chemical environment in a conventional ETS-10 synthesis mixture forces essentially all of the titanium into octahedral coordination to form titanium silicate chains so that direct synthesis, especially the controlled direct synthesis of mixed octahedral/tetrahedral sites is not achieved using conventional procedures.

Procedures for decreasing the overall Si/Ti ratio of titanium silicate sieves are not disclosed.

SUMMARY OF THE INVENTION

The invention relates to novel titanium silicate molecular sieve catalysts having both octahedral and tetrahedral titanium atoms in the framework. The counterions in the molecular sieve are predominantly in acid form, i.e., hydrogen or a cation such as ammonium ion that is thermally convertible to hydrogen ion. Thus, the catalysts contain both desirable acidic and oxidative sites.

Molecular sieves of this class are prepared by two general methods. In one, the sieves are prepared by partitioning titanium in a titanium silicate synthesis gel into both tetrahedrally and octahedrally coordinated atoms. The synthesis gel is one that would normally produce a crystalline molecular sieve with a chain-like structure in which all titanium is in octahedral coordination. Tetrahedral titanium takes positions normally occupied by silicon in the unmodified structure, resulting in a lower Si/Ti ratio. The resulting material is then ion-exchanged with hydrogen cations or a source thereof.

In another method, the crystalline molecular sieve containing substantially all titanium in octahedral coordination and tetrahedral silicon is synthesized, then exchanged with acid and thereafter treated with a reagent that replaces tetrahedral silicon atoms with tetrahedral titanium atoms.

While the preferred embodiments involves modification of the molecular sieve ETS-10 framework, the same principles may be applied to other molecular sieves including ETS sieves by substituting Ti(IV) for silicon into other known and possibly not presently known, crystalline titanium silicate sieves based on a chain-like titanium silicate framework, as exemplified by: ETS-4, ETAS-10 and ETS-14.

The art indicates that highly siliceous zeolites or molecular sieves that contain small amounts of tetrahedrally coordinated framework titanium atoms catalyze the selective oxidation of alkanes, alkenes and aromatics (e.g. phenol) in the presence of peroxide. For example, catalysts of this type are the basis for a commercial process for oxidation of phenol to catechol and hydroquinone.

The art also indicates that framework titanium in tetrahedral coordination is necessary for these oxidations. Since ETS-10 nominally contains no tetrahedrally coordinated titanium, it would be expected that ETS-10 would not catalyze the oxidation of organic compounds by peroxide. In fact, unmodified ETS-10 has little, if any, oxidation capability.

An unexpected result is that the products of the oxidation are different using modified ETS-10. Modified ETS-10 tends to oxidize carbons adjacent to double bonds or aromatic rings. For example, oxidation of ethylbenzene gives acetophenone whereas oxidation of ethylbenzene with peroxide and titanium substituted ZSM-5 (TS-1) gives ethylphenol.

Still, another unexpected result is that modified ETS-10 is a more substrate selective, milder oxidizing agent than prior art catalysts. For example, prior art catalysts oxidize phenol and alpha olefins. Modified ETS-10 does not. In contrast, prior art titanium based zeolite catalysts do not oxidize allylic carbons in the presence of peroxide. Modified ETS-10 catalysts do this oxidation.

Products of the Invention

Detailed Description

The invention relates to oxidation catalysts comprising a crystalline titanium silicate molecular sieve, comprising both di-charged octahedrally coordinated titanium atoms and tetrahedrally coordinated titanium atoms in the framework, wherein exchangeable cations in the molecular sieve are predominately hydrogen or cations such as ammonium ions that are thermally convertible to hydrogen cations.

In a presently preferred embodiment, the molecular sieve is based on ETS-10. Thus, the invention will be described with special emphasis on modified forms of ETS-10 molecular sieve. These modified forms have the x-ray diffraction of ETS-10 and a Si/Ti molar ratio (bulk ratio) in the range of 2 to 5.

In a preferred embodiment, the molar Si/Ti ratio in the modified ETS-10 type containing both octahedrally and tetrahedrally coordinated titanium atoms is less than 5, preferably above 3, and most preferably above 4. Typically, the Si/Ti ratio is in the range of 3.5 to 4.7.

Products of the invention (herein referred to as Ti/ETS-10) contain the most significant line which are set forth in Table 1.

TABLE 1

CHARACTERISTIC XRD d-SPACINGS OF Ti/ETS-10

| d-SPACING (ANGS.) | I/I$_0$ |
|---|---|
| 14.7 ± 0.35 | W–M |
| 7.20 ± 0.15 | W–M |
| 4.41 ± 0.10 | W–M |
| 3.60 ± 0.05 | VS |
| 3.28 ± 0.05 | W–M |

Wherein
VS = 50–100
W–M = 15–50

The d-spacings reported in Table 1 are the significant lines for ETS-10. However, products of the invention can be readily distinguished from known forms of ETS-10. The first X-ray peak at 14.7±0.35 and the strongest peak at 3.60±0.05 are slightly higher than classical ETS-10 and are consistent with the substitution of slightly larger Ti(IV) for a portion of the tetrahedral Si(IV) units. Also, the IR (infra-red) spectrum of certain products of the invention distinguish from ETS-10.

Spectra of both contain silicon stretching bands at a 1030 cm$^{-1}$ wave number as the strongest feature in the spectrum. In ETS-10 there is essentially no peak in the region of 1000–900 wave numbers and in the acid exchanged material there is a very small peak in the 960–980 region. In contrast, for as synthesized Ti/ETS-10, wherein tetrahedral titanium is introduced during synthesis, there is a very large peak at approximately 980 cm$^{-1}$ where there is no peak in as synthesized ETS-10. In addition, the infra-red spectrum of the acid form of Ti/ETS-10 has a very large peak at approximately 975 cm$^{-1}$ whereas there is a small peak in acid exchanged ETS-10. Furthermore, catalytic data shown in the accompanying examples confirm differences from ETS-10. In the scientific literature, the exact assignment of the IR peak at the 980 cm$^{-1}$ wave number is a matter of some controversy. However, it is more or less universally regarded as an indication of the modification of a molecular sieve high silicon framework by inclusion of heteroatoms such as titanium. For example, this peak is diagnostic for inclusion of Ti into the framework of ZSM-5 to give the sieve TS-1. Thus, the presence of this infra-red peak along with the catalytic activity of Ti/ETS-10 is very strong evidence that the framework of ETS-10 has been changed by the inclusion of Ti into silicon sites and the two materials are substantively different.

While all scientific evidence to date is that the nonoctahedral titanium position of products of the invention is tetrahedral, it is possible that during use in reactions such as oxidative catalysis, the titanium may assume other configurations such as penta or hexa coordination or combination.

Preparation of Catalyst by Direct Gel Synthesis

Detailed Description

The novel titanium silicate molecular sieve catalysts of this invention having a Si/Ti ratio less than 5 can be prepared by modification of a conventional gel synthesis mixture for preparing ETS-10 molecular sieve by adding a chelating agent for octahedral titanium atoms, preferably a peroxide, most preferably hydrogen peroxide, to such mixture prior to gelation and crystallization. Other peroxides include water soluble peroxides such as sodium peroxide, organic peroxide such as t-butyl peroxide, cyclohexyl peroxide, sodium percarbonates, peroxidisulfates, and peroxy compounds such as dialkyl peroxides and alkyl peroxy esters mixtures can be used. The chelating agent must be capable of complexing octahedral titanium atoms to form titanium atoms having tetrahedral coordination and keep them in such coordination state prior to crystallization so that a significant fraction of silicon atoms are replaced by tetrahedral Ti atoms in the tetrahedral silicon containing chains that make-up ETS-10. In effect, the titanium reservoir in the ETS-10 synthesis mixture is partitioned into tetrahedrally and octahedrally coordinated atoms which are incorporated into their respective chains. The net effect is that some Ti atoms replace Si atoms in the tetrahedral chain and the resulting structure is ETS-10-like with a lower Si/Ti ratio. Typical pore size is about 8 Angstrom units.

The mole ratio of chelating agent to TiO$_2$ is generally from 0.1 to 50, preferably from 0.5 to 10, and most preferably about 0.5. Preferably the atomic Si/Ti ratio (total) is from 2 to 20, most preferably 2 to 7. If too little peroxide is added, insufficient tetrahedral titanium is present in the crystallized product.

As mentioned, catalysts of the invention can be prepared by modification of a conventional gel synthesis mixture for preparing ETS-10 molecular sieve. Such conventional synthesis utilizes a reaction mixture containing a titanium source such as titanium trichloride, a source of silica, a source of alkalinity such as an alkali metal hydroxide, water and, optionally, an alkali metal fluoride mineralizer having a composition in terms of mole ratios falling within the range set forth in Table 2.

TABLE 2

CONVENTIONAL COMPOSITION OF REACTANTS TO PREPARE ETS-10 BY GEL SYNTHESIS

| | Broad | Preferred | Most Preferred |
|---|---|---|---|
| $SiO_2/Ti$ | 2–20 | 2–10 | 2–7 |
| $H_2O/SiO_2$ | 2–100 | 5–50 | 10–25 |
| $M_a/SiO_2$ | 0.1–20 | 0.5–5 | 1–3 | wherein "M" indicates the cations derived from the alkali metal hydroxide and fluoride and/or alkali metal salts used for preparing the titanium silicate according to the invention and "a" is the valence of M. To the reaction mixture the chelating agent, preferably hydrogen peroxide, is added in order to prevent all titanium from entering octahedral coordination. The reaction mixture is heated to a temperature of from about 100° C. to 250° C. for a period of time ranging from about 2 hours to 40 days, or more. The hydrothermal reaction is carried out until crystals are formed and the resulting crystalline product is thereafter separated from the reaction mixture, cooled to room temperature, filtered and water washed. The reaction mixture can be stirred although it is not necessary. It has been found that when using gels, stirring is unnecessary but can be employed. When using sources of titanium which are solids, stirring is beneficial. The preferred temperature range is 150° C. to 225° C. for a period of time ranging from 4 hours to 7 days. Crystallization is performed in a continuous or batchwise manner under autogenous pressure in an autoclave or static bomb reactor. Following the water washing step, the crystalline ETS-10 is dried at temperature of 100° to 600° F. for periods up to 30 hours.

Prior to crystallization, the gel resulting from the reaction mixture can be subjected to one or more thermal treatments at temperature of from about 150° C. to 800° C. for 1–48 hours. The thermally treated gel is mixed with water and crystallized.

Quite obviously, it is possible to use less caustic, or other reactants in the gel than set forth in Table 2 and supply these during the crystallization step after the gel has been thermally treated.

The silica source includes most any reactive source of silicon such as silica, silica hydrosol, silica gel, silicic acid, alkoxides of silicon, alkali metal silicates, preferably sodium or potassium, or mixtures of the foregoing.

The titanium oxide source can be a trivalent or tetravalent and compound. Examples include titanium trichloride, titanium sulfate or oxysulfate, $TiCl_3$, titanium tetrachloride, $TiCl_4$, and titanium oxychloride, $TiOCl_2$.

The source of alkalinity is preferably an aqueous solution of an alkali metal hydroxide, such as sodium hydroxide, which provides a source of alkali metal ions for maintaining electrovalent neutrality and controlling the pH of the reaction mixture within the range of ~10.0 to 12.0 using the technique elaborated upon in U.S. Pat. No. 4,853,202. The alkali metal hydroxide serves as a source of sodium oxide which can also be supplied by an aqueous solution of sodium silicate.

The exchangeable cations in the crystallized product are usually Na and K. To produce acidic catalysts, it is essential to extensively replace these alkali metal cations with hydrogen ion or precursors thereof such as ammonium ion followed by calcination in known manner. Preferably, the maximum amount of total alkali metal cations in the exchanged product is less than 55% and is most preferably minimal, for example $(Na_2O+K_2O)<2.5$ wt. % based on the volatile free weight. However, unlike other oxidation catalysts based on molecular sieves or zeolites, the products of this invention can tolerate moderate quantities of alkali metals.

Because the products of the invention contain a unique combination of acid sites as well as tetrahedrally coordinated titanium sites, they are uniquely adapted for catalytic applications in which both type of sites are desirable, for example converting olefins to diols.

Typically, well-washed prior art forms of ETS-10 have a Si/Ti ratio in the range of 4.8 to 5.2/1 (U.S. Pat. No. 4,853,202). Typical products of the invention obtained by modification of gel synthesis have a Si/Ti ratio of 4.7 or less Thus, the formula for a typical hydrogen form of compositions of the invention expressed as oxides is typically as follows:

$$(1.0\pm0.25)MO_{2/a}:TiO_2:(3-4.5)SiO_2:(4.0\pm0.3)H_2O$$

wherein at least 65% of M is $H^+$ and the balance of M is sodium, potassium or mixture thereof, and "a" is the valence of M.

XRD analysis of products of this invention contain at least the significant line set forth in Table 1 (supra).

As mentioned, products of the invention can be readily distinguished from known forms of ETS-10. The first x-ray peak at 14.7±0.35 and the strongest peak at 3.60±0.05 are slightly higher than classical ETS-10 and are consistent with the substitution of slightly larger (Ti(IV)) for a portion of the tetrahedral Si(IV) units. Also, the IR spectrum of products of the invention obtained during direct synthesis distinguish it from ETS-10. Spectra of both contain silicon stretching bands of 1030 wave number as the strongest feature in the spectrum. However, the peak at 980 wavelength, indicative of tetrahedral titanium, is completely absent from the spectrum for conventional ETS-10 but is readily apparent in the spectrum for products of the invention. Furthermore, catalytic data shown in the accompanying examples confirm differences from ETS-10.

Preparation of Catalyst by Post Synthesis Chemical Modification

Detailed Description

In another embodiment, a molecular sieve such as ETS-10 is acid exchanged by methods well known in the art of zeolites and molecular sieves. The resulting "acidic form sieve" is then treated with a solution of a chemical reagent such as ammonium titanium hexafluoride, (ATH), $(NH_4)_2TiF_6$, which we believe removes tetrahedral or octahedral atoms from the molecular sieve framework, leaving in effect a hole or vacancy in the framework structure. The hole is then filled by the titanium atoms from solution. If an octahedral titanium atom is removed from the ETS-10 structure, it is then replaced a titanium atom from solution and no net change occurs. However if a silicon atom is removed from the structure it is replaced by a titanium atom. The net result is the substitution of titanium for silicon in the siliceous tetrahedral chains of ETS-10. As a result the Si/Ti atomic ratio of the treated ETS-10 is decreased. Alternatively we have found that this method is useful for inserting heteroatoms other than Ti into the structural chains of ETS-10. Thus for example, treating ETS-10 with $(NH_4)_yXF_6$, where X is a "heteroatom" including but not limited to such atoms as Ta or Fe, can result in the incorporation of such element into the ETS-10 framework.

Not unexpectedly, the conditions of the sieve treatment by ATH can affect the degree and efficacy of Ti incorporation into the molecular sieve.

There are a number of parameters to control including:
- ratio of solid/liquid in the molecular sieve slurry;
- the pH of the slurry;
- the temperature of the slurry during ATH addition;
- the rate of ATH addition;
- the amount of ATH added relative to the sieve;
- time and temperature of treatment after ATH addition is complete;
- degree of washing.

We have found that the ratio of solid to liquid in the molecular sieve slurry can vary considerably, e.g., from 1 to 40% solids. The preferred range is approximately 5 to 20% solids and the most preferred range is approximately 5 to 15% solids. The pH of the slurry prior to treatment should be acid. The preferred range for pH is approximately 6.9 to 2. The most preferred pH range is approximately 6 to 3.

The temperature of the slurry during treatment with ATH can vary considerably depending on the desired rate of reaction. In general, the temperature range for the treatment is approximately 25 to 100° C. A preferred range is 25 to 80° C. The most preferred range is 40 to 80° C.

The rate of ATH addition will affect the rate of reaction and may affect the uniformity of the product obtained. In general, it is preferable to add the ATH as slowly as practical.

The amount of ATH added also will affect the rate of reaction and the amount of Ti substitution obtained. In general, the weight ratio of ATH to sieve (based on the volatile free weight of the sieve) will be in the 0.01 to 0.40 range. A preferred range is 0.5 to 0.30 and the most preferred range is 0.10 to 0.30.

The time and temperature of treatment post addition of ATH will be a function of the other parameters of the reaction (e.g., time, concentrations, ATH/sieve). In general more dilute concentration require a longer time. It is generally advisable to react the sieve for a period of hours, for example 1–24, after addition of ATH is complete.

It is important to wash the sieve well after reaction treatment is complete. This removes unreacted Ti, Si debris and fluoride salts from the sieve.

It should be understood that the conditions of treatment of titanium silicate sieves with ATH to achieve tetrahedral titanium incorporation can span a wide range and are dependent upon the result desired. While the conditions specified here are representative they are not intended to be comprehensive.

The following examples are incorporated for illustrative purposes and are not to be construed as limiting the invention to the specific embodiments described therein.

EXAMPLE 1

In this example, illustrating practice of the invention utilizing modification of conventional gel synthesis, the reactants and procedures described in U.S. Pat. No. 5,208,006 at col. 18 est. seq., were employed except that the source of titanium was titanium oxychloride (20 wt. % $TiO_2$). The hydrogen peroxide was 30 wt. % $H_2O_2$ in water.

The following reactants solutions were prepared:
Solution 1) 300 grams of $Na_2SiO_3$ (N-Brand) were dissolved in 120 grams deionized $H_2O$.

Solution 2) 14.4 grams of NaOH were dissolved in 120 grams deionized $H_2O$.

Solution 3) 20.4 grams of KOH were dissolved in 120 grams deionized $H_2O$.

Solution 4) 96.0 grams of $TiOCl_2$ were dissolved in 120 grams of deionized $H_2O$.

Solution 5) 20.0 grams of $H_2O_2$ (30%) were dissolved in 120 grams deionized $H_2O$.

The reactants were combined by first adding solution 2 to solution 1. To this mixture solution 3 was added and blended. The titanium source of solution 4 was added and blended. Finally, the complexing peroxide was added as solution 5. The resulting gel was lightly yellow colored, with a pH measuring 10.5. This gel was crystallized at 200 degrees C. for 18 hours., much as would be typical for an analogous ETS-10 mixture, filtered, washed with deionized H2O, and dried at 120 degrees C. for three hours.

X-ray diffraction was determined on air equilibrated samples using the equipment and procedures set forth in U.S. Pat. No. 5,208,006, col. 6, I. 55 et. seq. XRD patterns qualitatively similar to ETS-10 were obtained. However, the first peak at 14.87 Angstroms, and the strongest peak at 3.61 Angstroms, are slightly but significantly higher than classical ETS-10, and are consistent with the substitution of slightly larger Ti(IV) for a portion of the tetrahedral Si(IV) units. Pore size was 8 Angstrom as determined by XRD (based on lead peak) and structural modeling procedures.

EXAMPLE 2

A sample of the product of Example 1 was subjected to IR analysis. FTIR experiments was performed using BIO-RAD-FTS-60 Spectrometer. Transparent disc was prepared with about 200 mg of mixture containing KBr (97 wt. %) and (3% wt. %) sample of product of this invention. The spectrum was recorded between 1500 and 400 $cm^{-1}$, under normal conditions (20° C., ATM pressure in room air).

The largest feature of the spectrum was found to be a doublet centering at approximately 1030 and 980 wave numbers. The peak at 1030 is generally attributed to silicon stretching in a zeolite framework. The peak at 980 is often attributed to tetrahedral titanium substituted into the framework of classical zeolites. This pattern is therefore consistent with a high degree of tetrahedral titanium (IV) substitution into the zeolite-like ETS-10 framework.

EXAMPLE 3

In order to contrast the IR spectrum of standard ETS-10 with the product of Example 1, a sample of commercial as synthesized desiccant grade ETS-10 supplied by Engelhard corporation was subjected to IR analysis. In this case, while the silicon stretching peak at 1030 $cm^{-1}$ wave numbers was again the strongest feature in the spectrum; the peak at 980 $cm^{-1}$, indicative of tetrahedral titanium, was completely absent.

This contrasts strongly with the spectrum of Example 2 and noting the equivalence of crystalline structure as indicated by the similarity of XRD patterns offer strong evidence for the incorporation of substantial tetrahedral titanium in the crystal structure of the product of Example 1.

EXAMPLE 4

Molecular sieves containing tetrahedral titanium are well known catalysts for epoxidation reactions. Large-pored titanium containing zeolites such as substituted Zeolite Beta are able to accommodate movement of cyclohexene and its derivatives easily through the pore structure while intermediate-pored ZSM-5 derivatives, such as TS-1, are subject to substantial steric hindrances. Thus, a test of whether active tetrahedral titanium(IV) sites are present within a crystal of large-pored molecular sieve can be made by the epoxidation of cyclohexene. TS-1 is essentially inert in this reaction while substituted Zeolite Beta is quite active. In order to assess whether the acid form of the product of Example 1 has active internal sites, a sample of the product of Example 1 was hydrogen exchanged at a pH of approximately 1.8 in hydrochloric acid. Twenty-four (24) grams of acetonitrile, 1.0 gram of 30% hydrogen peroxide solution and 2.7 grams of cyclohexene were placed in a round bottom flask with a condenser and a stirring bar and heated to exchanged, was added and the resulting slurry was heated for four hours. After cooling reflux. 0.5 grams of the material of Example 1, which had been hydrogen, titration showed 86% of the peroxide was gone. GC-MS analysis (ion-chromatogram) indicates approximately 23% conversion of cyclohexene with the following selectivities based on cyclohexene:

| | |
|---|---|
| 2-cyclohexen-1-ol | 22% |
| 2-cyclohexenenone | 22% |
| 1,2-cyclohexanediol | 39% |
| others | 17% |

This demonstrates that titanium sites are active within the crystals of the material. It should be noted that H-ETS-10, which has been hydrogen exchanged but not severely enough treated to extract framework titanium, shows essentially no activity for this reaction. In order to demonstrate that this new material possesses sites very different from acid modified ETS-10, the following experimental work was conducted:

EXAMPLE 5

The conditions of Example 4 were repeated except that 2.2 grams of 1-hexene were used instead of cyclohexene. After four hours of reaction time, titration showed that 0% of the starting peroxide remained. GC-MS analysis indicated a single oxidation product, 1,2 hexanediol. It is clear that the selectivity to oxidation products based on peroxide was very high; i.e., the oxidation reaction seemed to be very selective. We assume that the initial oxidation product was the epoxide which undergoes solvolysis to the diol. This experiment offers strong evidence that the acid form of the product of Example 1 contains active tetrahedral titanium. In contrast, the acid-extracted ETS-10 reacted under the same conditions gives no 1-hexene oxidation products.

EXAMPLE 6

This example illustrates the preparation of Ti/ETS by post-synthesis treatment with ATF. H$^+$ ETS-10 was prepared by repetitive acid exchange of as-synthesized ETS-10 with hydrochloric acid. The chemical analysis of the resulting product was as follows (all analyses are wt % on VF (volatile free) basis):

| | |
|---|---|
| K$_2$O | 3.56 |
| Na$_2$O | 1.07 |
| SiO$_2$ | 75.8 |

-continued

| | |
|---|---|
| TiO$_2$ | 19.5 |
| Si/Ti | 5.18 |

10.5 g of H+ETS-10 was slurried in 80 ml water. The resulting pH was approximately 6. The slurry was heated to 60° C. Then 2.5 g of ammonium titanium hexafluoride was added in two portions. The resulting mixture was stirred and heated for 6 h. Then the slurry was cooled and filtered. The solid was reslurried in approximately 100 ml water. After stirring for 0.5 h the solid material was filtered. The solid was reslurried in approximately 100 ml of water. After stirring for 0.5 h, the solid material was filtered. The filter cake was air dried and then dried in an oven at 90° C. for at least 2 h.

The chemical analysis of the resulting product was as follows (all analyses are wt % on a volatile free (VF) basis):

| | |
|---|---|
| K$_2$O | 2.1 |
| Na$_2$O | 0.2 |
| SiO$_2$ | 73.4 |
| TiO$_2$ | 24.3 |
| LOI | 13.75 |
| Si/Ti | 4.0 |

Infra-red analysis of the product showed an enhanced peak at approximately 980 cm$^{-1}$. This is indicative of insertion of Ti in framework positions in ETS-10. The Raman spectrum of the product from this example shows the same features as H+ETS-10 with one prominent exception. A major Raman peak for H+ETS-10 normally occurs between 800–850 cm$^{-1}$. In the product of Example 6, this peak has a different shape and occurs at 775 cm$^{-1}$. This result suggests a subtle structural change in the ETS-10 framework.

SEM analysis indicates large well defined crystals and that no amorphous material is present.

Further evidence of the presence of Ti in tetrahedral framework sites is given by Example 7.

EXAMPLE 7

Zeolites which contain a significant amount of tetrahedral titanium (e.g., TS-1, TS-2, Ti-Beta) oxidize olefins such as 1-hexene to the corresponding epoxide or diol in the presence of hydrogen peroxide. In contrast H$^+$ETS-10, which presumably has little or no tetrahedral titanium, gives no detectable 1-hexene oxidation products in the presence of peroxide. 24 g acetonitrile (Aldrich HPLC grade), 1.0 g of 30% hydrogen peroxide solution, (Baker analyzed) and 2.2 g of 1-hexene (Aldrich) were placed in a round bottom flask with a stirring bar and heated to reflux. 5 g of the material from Example 6 was added and the resulting slurry was heated for 4 h. After cooling titration showed that all the peroxide had reacted. GC-MS analysis indicated only two oxidation products. The primary product was the epoxide of 1-hexene. The minor product was 1,2 hexanediol. It is highly likely that 1,2hexanediol comes from reaction of the epoxide with water present in the reaction mixture from the aqueous hydrogen peroxide solution. The approximate ratio of epoxide to diol was 6:1.

These results are strong evidence that a significant amount of tetrahedral Ti was incorporated into ETS-10.

Examples 8 and 9 show that the amount of Ti that is incorporated into ETS-10 by chemical treatment can be easily controlled using ATH.

EXAMPLE 8

A slurry of 40 g of H+ETS-10 (Example 6) in 300 ml of water was adjusted to a pH of 3.5 with dilute nitric acid. 10.2 g of ammonium titanium hexafluoride was dissolved in 75 ml water. After heating the slurry to 40° C. the solution of the ATH was added to the slurry in small portions over 1 h. The resulting mixture was heated and stirred for 5 h. It was then filtered. The filter cake was washed well with water and then redispersed in 300–400 ml water. The slurry was filtered and the resulting solid was dried at 90° C. for at least 2 h. The chemical analysis of the resulting product was as follows (wt % on VF basis):

| | |
|---|---|
| LOI | 13.5 |
| $K_2O$ | 2.1 |
| $Na_2O$ | 0.5 |
| $SiO_2$ | 74.1 |
| $TiO_2$ | 23.3 |
| Si/Ti | 4.24 |

The Si/Ti ratio decreased from 5.2 (starting material) to 4.24 indicating increased Ti in the ETS-10 structure. The infra-red spectrum had an enhanced peak at 980 cm-1, indicating incorporation of Ti into the ETS-10 framework.

EXAMPLE 9

10 g of the product from Example 6 was slurried in 60 ml water. 2.5 g of ATH was dissolved in 20 ml water. The slurry was heated to 60° C. and over a period of 1 h the ATH was added to the slurry using a syringe pump. The resulting mixture was heated and stirred for 6 h. It was then filtered. The filter cake was washed with 100 ml water and redispersed in 100 ml water. After filtration the solid material was dried at 90° C. for at least 2 h.

The chemical analysis of the resulting product was as follows: (wt % on VF basis):

| | |
|---|---|
| LOI | 13.5 |
| $K_2O$ | 1.4 |
| $Na_2O$ | 0.15 |
| $SiO_2$ | 70.85 |
| $TiO_2$ | 27.6 |
| Si/Ti | 3.42 |

The decreasing Si/Ti ratio indicate that even more of the Si was replaced with Titanium. X-ray analysis indicates that the ETS-10 structure is intact.

We claim:

1. An oxidation catalyst comprising a crystalline titanium silicate molecular sieve having exchangeable cation sites and containing both octahedrally coordinated titanium atoms and tetrahedrally coordinated titanium atoms in the framework, wherein the exchangeable cations are predominantly hydrogen or a cation thermally decomposable to hydrogen.

2. The catalyst of claim 1 wherein said titanium silicate is of the ETS-10 type.

3. The catalyst of claim 1 which has a chain-like titanium silicate framework in which the majority of the titanium atoms are octahedrally coordinated and a minor amount are tetrahedrally coordinated.

4. The catalyst of claim 3 which has the x-ray pattern of ETS-10 titanium silicate.

5. The catalyst of claim 4 which has an IR peak at 980 $cm^{-1}$.

6. The catalyst of claim 5 which has a Si/Ti ratio below 5.

7. The catalyst of claim 6 which has a Si/Ti ratio above 3.

8. The catalyst of claim 6 which has a Si/Ti ratio of about 4.

9. The catalyst of claim 1 wherein more than 65% of the exchangeable cations are hydrogen.

10. The catalyst of claim 9 wherein the titanium silicate has the x-ray pattern of ETS-10.

11. The catalyst of claim 1 wherein the titanium silicate is defined by the formula: $(1.0\pm0.25)M_{2a}O:TiO_2:2-5 SiO_2:2.5-5 H_2O$ wherein at least about 65% of M is H, the remainder being Na, K or combinations thereof, and "a" is the valence of M.

12. An oxidation catalyst containing both acidic and oxidation sites which is a porous hydrogen form titanium molecular sieve silicate based on a framework of a di-charged octahedrally coordinated titanium atoms and tetrahedrally coordinated silica atoms and contains a minor amount of tetrahedrally coordinated titanium atoms in the framework.

13. The catalyst of claim 12 which has the x-ray pattern of ETS-10 and has an IR peak at 980–950 $cm^{-1}$.

14. A method for preparing a modified form of the crystalline molecular sieve ETS-10 which comprises mixing at least one water soluble peroxide with a reaction mixture capable of producing ETS-10 in the absence of said peroxide and recovering the resulting modified ETS-10 crystals.

15. The method of claim 14 which comprises mixing an aqueous acidic solution of a source of titanium ions with an aqueous alkaline solution of sodium silicate in proportions selected to form ETS-10 crystals, adding a water soluble peroxide to the mixture either before or after reaction takes place between the source of titanium ions and sodium silicate and heating the resulting mixture containing said peroxide until crystals of modified ETS-10 containing both octahedrally and tetrahedrally coordinated titanium atoms form, and washing and thereafter ion-exchanging the crystals with hydrogen or a source of hydrogen ions to replace alkali metal ion.

16. A method for preparing a titanium silicate oxidation catalyst containing both discharged octahedrally coordinated titanium atoms and tetrahedrally coordinated silicon atoms which comprises extracting silica from a crystalline titanium silicate molecular sieve at an acidic pH with a reagent that selectively replaces tetrahedral silicon atoms with tetrahedral titanium atoms.

17. The method of claim 16 wherein said reagent is ammonium titanium hexafluoride.

18. The method of claim 16 wherein reagent is $(NH_4)yXF_6$ wherein X is a heteroatom and y is the valence of X-6.

19. A method for oxidizing an organic compound which comprises treating at least one organic compound in the presence of peroxide with the catalyst of claim 1.

* * * * *